United States Patent [19]

Gallegra et al.

[11] Patent Number: 5,175,348
[45] Date of Patent: Dec. 29, 1992

[54] PROCESS FOR THE PREPARATION OF HALOGENATED CARBOXYLIC ACID ESTERS

[75] Inventors: Pasquale Gallegra, Muttenz; Gerhard Degischer, Füllinsdorf, both of Switzerland

[73] Assignee: Säurefabrik Schweizerhall, Schweizerhalle, Switzerland

[21] Appl. No.: 849,573

[22] Filed: Mar. 10, 1992

[30] Foreign Application Priority Data

Mar. 11, 1991 [CH] Switzerland .................. 716/91

[51] Int. Cl.$^5$ .............................................. C07C 67/02
[52] U.S. Cl. ........................ 560/266; 560/223; 560/111; 560/125; 560/56; 560/421; 560/100; 560/179; 560/126; 560/64; 560/156
[58] Field of Search ............ 560/266, 223, 111, 125, 560/56, 21, 100, 179, 126, 64, 156

[56] References Cited

U.S. PATENT DOCUMENTS 3,697,507 10/1972 Frederiksen et al. ............ 260/239.1
3,850,908 11/1974 von Daehne et al. ............ 260/239.1

FOREIGN PATENT DOCUMENTS 0083484 7/1983 European Pat. Off. .
0406660 1/1991 European Pat. Off. .
1951012 4/1970 Fed. Rep. of Germany .
2269508 11/1975 France .
1313850 5/1987 U.S.S.R. .
2152504 8/1985 United Kingdom .

OTHER PUBLICATIONS

Grynkiewicz et al., Polish Journal of Chemistry, vol. 61 (1987) pp. 443–447.
Binderup et al., Synthetic Communications, vol. 14, No. 9 (1984) pp. 857–864.
Rasmussen et al., J. Amer. Chem. Soc., vol. 89, No. 21 (1967) pp. 5439–5445.
Wheeler et al., J. Med. Chem., vol. 22, No. 6 (1979) pp. 657–661.
Euranto et al., Acta. Chem. Scand., vol. 20 (1966) pp. 1273–1280.
Neuenschwander et al., Helv. Chim. Acta., vol. 60 (1977) pp. 1061–1072.
Ulich et al., J. Amer. Chem. Soc., vol. 43 (1921) pp. 660–667.
Kochhar et al., J. Org. Chem., vol. 48 (1983) pp. 1765–1767.
Olah et al., Synthesis, Nov. 1982, pp. 962–963.
Michie et al., Synthesis (1981), p. 824.

Primary Examiner—Paul J. Killos
Attorney, Agent, or Firm—Wenderoth, Lind & Ponack

[57] ABSTRACT

The invention relates to a novel process for the preparation of halogenated carboxylic acid esters of formula I

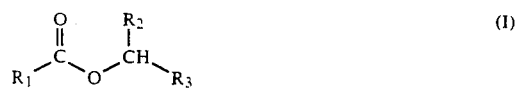

wherein $R_1$ is alkyl, alkenyl, alkynyl, cycloalkyl, aralkyl or aryl, $R_2$ hydrogen is alkyl or cycloalkyl, and $R_3$ is halogen having an atomic number of from 9 up to and including 53, which process comprises reacting an acylal of formula II

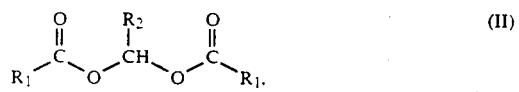

with a hydrogen halide of the formula H—$R_3$ (III).

14 Claims, No Drawings

PROCESS FOR THE PREPARATION OF HALOGENATED CARBOXYLIC ACID ESTERS

The invention relates to a novel process for the preparation of halogenated carboxylic acid esters of formula I

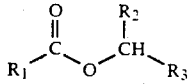 (I)

wherein $R_1$ is alkyl, alkenyl, alkynyl, cycloalkyl, aralkyl or aryl, $R_2$ hydrogen is alkyl or cycloalkyl, and $R_3$ is halogen having an atomic number of from 9 up to and including 53, which process comprises reacting an acylal of formula II

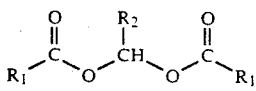 (II)

with a hydrogen halide of the formula

 (III).

Alkyl is preferably lower alkyl, such as straight-chained or branched $C_1$–$C_7$alkyl, such as methyl, ethyl, propyl, isopropyl, butyl, isobutyl, sec-butyl, tert-butyl, pentyl, isopentyl, sec-pentyl, neopentyl or a hexyl or heptyl group, but it may also be a $C_8$–$C_{14}$alkyl group, such as an octyl, nonyl or decyl group. In the case of $R_1$ preference is given to methyl, ethyl and also secondary-linear and branched $C_3$–$C_7$alkyl groups, such as isopropyl, but-2-yl, pent-3-yl, tert-butyl or 2-methylbut-2-yl, and in the case of $R_2$ preference is given to linear $C_1$–$C_4$alkyl groups, such as methyl, ethyl, propyl or butyl.

Alkenyl is preferably straight-chained or branched $C_2$–$C_7$alkenyl, such as ethenyl, propenyl, for example allyl, isopropenyl, methallyl (crotyl), butenyl or 2-methylprop-2-enyl.

Alkynyl is, for example, $C_3$–$C_7$alkynyl, such as propargyl.

Cycloalkyl is, for example, 3- to 8-membered, such as 5- to 7-membered, cycloalkyl, for example cyclopropyl, cyclobutyl, cyclopentyl, cyclohexyl or cycloheptyl.

Aryl is, for example, phenyl or naphthyl; aralkyl is, for example, mono-, di- or tri-phenyl-$C_1$–$C_4$alkyl, such as benzyl, 1-phenylethyl, diphenylmethyl or triphenylmethyl. Phenyl and naphthyl and the phenyl moiety of mono-, di- or tri-phenyl-$C_1$–$C_4$alkyl may be unsubstituted or substituted, such as mono-, di- or tri-substituted, by customary substituents, such as lower alkyl, for example methyl, lower alkoxy, for example methoxy, halogen, for example chlorine or bromine, trifluoromethyl and/or nitro, but they are preferably unsubstituted.

Halogen having an atomic number of from 9 up to and including 53 is, for example, chlorine or bromine, but may, secondly, also be iodine.

Unless indicated otherwise, the expression "lower" used in the definition of radicals such as lower alkyl and lower alkoxy means that the radicals concerned contain up to and including 7, preferably up to and including 4, carbon atoms.

The compounds of formula I are valuable intermediates in organic synthesis, especially for the preparation of active ingredients for medicaments. They react with amines, alcohols and carboxylic acids with the introduction of the group of the formula

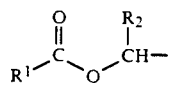 (Ia)

to form the corresponding substituted amines, ethers and esters. The compounds of formula I are suitable especially for the preparation of corresponding acyloxyalkyl esters of β-lactam antibiotics, such as penicillins, for example 6-[D-(−)-α-aminophenylacetamido]-penicillanic acid (pivaloyloxy)methyl ester hydrochloride (Pivampicillin), and of cephalosporins, for example 7-[(2-amino-4-thiazolyl)-(methoxyiminoacetylamino)-3-methyl-8-oxo]-5-thia-1-azabicyclo[4.2.0]octenecarboxylic acid (pivaloyloxy)methyl ester (Cefetamet pivoxil) and the like.

The invention relates especially to the preparation of compounds of formula I wherein $R_1$ is $C_1$–$C_{14}$alkyl, $C_2$–$C_7$alkenyl, $C_3$–$C_7$alkynyl, or 3- to 8-membered cycloalkyl; or is phenyl or naphthyl each of which is unsubstituted or substituted by $C_1$–$C_4$alkyl, $C_1$–$C_4$alkoxy, halogen, trifluoromethyl and/or by nitro, or mono-, di- or tri-phenyl-$C_1$–$C_4$alkyl that is unsubstituted or substituted in the phenyl moiety by $C_1$–$C_4$alkyl, $C_1$–$C_4$alkoxy, halogen, trifluoromethyl and/or by nitro, $R_2$ hydrogen is $C_1$–$C_7$alkyl or 3- to 8-membered cycloalkyl, and $R_3$ is halogen having an atomic number of from 9 up to and including 53.

The invention relates very especially to the preparation of compounds of formula I wherein $R_1$ is $C_1$–$C_7$alkyl, such as methyl or tert-butyl, $R_2$ is hydrogen or $C_1$–$C_4$alkyl, and $R_3$ is chlorine or bromine.

The invention relates preferably to the preparation of compounds of formula I wherein $R_1$ is methyl, ethyl or secondary-linear or branched $C_3$–$C_7$alkyl, such as isopropyl or tert-butyl, $R_2$ is hydrogen or, secondly, linear $C_1$–$C_4$alkyl, such as methyl or ethyl, and $R_3$ is chlorine or, secondly, bromine.

The invention relates most especially to the preparation of compounds of formula I wherein $R_1$ is methyl, ethyl or secondary-linear or branched $C_3$–$C_7$alkyl, such as isopropyl or tert-butyl, $R_2$ is hydrogen and $R_3$ is chlorine.

The invention relates specifically to the preparation of the compounds of formula I mentioned in the Examples, especially of chloromethyl pivalate ($R_1$=tert-butyl, $R_2$=hydrogen).

The customary process for the preparation of compounds of formula I comprises condensing an acid halide of formula IV

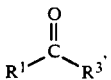 (IV)

wherein $R_1$ is methyl or tert-butyl and $R_3$ is chlorine or bromine, with paraformaldehyde in the presence of an appropriate zinc halide, or reacting an approximately equimolar mixture of an appropriate aldehyde of formula V $R_2$—CH=O (V)

and an acid of formula VI

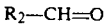

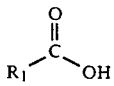
(VI)

with an excess of a thionyl halide of the formula $SO_2(R_3)_2$. Both variants of this process have decided disadvantages. In particular, it is known that the product obtained according to the first variant is in all cases contaminated by approximately 10 mol-% of the corresponding bis($\alpha$-haloalkyl)ether, and a considerably larger amount of that compound is formed according to the second variant, as is shown by the Comparison Example. However, owing to their toxicity, which especially in the case of the lower homologues of the group is very high, bis($\alpha$-haloalkyl)ethers give rise to considerable toxicological safety problems. That undesired by-product can be separated off only with great difficulty and can be removed virtually completely only at great expense. Moreover, in addition to sulfur dioxide and hydrogen chloride, a large number of other by-products is always formed; according to the first variant, for example, acylal acetals of formula VII

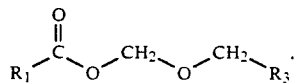
(VII)

anhydrides of formula VIII

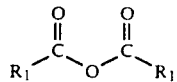
(VIII)

and acylals of formula II are formed, and according to the second process variant acid chlorides of formula IV are formed. These by-products, as well as excess aldehyde of formula V, make isolation of the desired product considerably more difficult.

For that reason, there has been no lack of attempts to develop processes for the preparation of compounds of formula I that avoid the mentioned disadvantages. However, the proposed solutions that have hitherto been disclosed are also toxicologically unacceptable, or are too expensive or too complex for industrial application.

For example, it has been proposed to react the acid of formula VI in the form of an alkali metal salt with an appropriate chlorosulfonic acid ($\alpha$-chloro)alkyl ester of formula IX

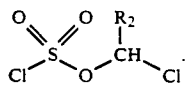
(IX)

However, reagents of formula IX are not very stable and, on account of their high toxicity, they in turn give rise to considerable toxicological safety problems, which prevent the use of this process on an industrial scale.

In accordance with another proposal, methylene diacetate or methylene dibenzoate (II; $R_1$=methyl or phenyl, $R_2$=hydrogen) is reacted with trimethylbromosilane in the presence of a 0.05- to 0.1-fold molar amount of a zinc halide, or with trimethylchlorosilane at 120° C. in the presence of a 0.2-fold molar amount of aluminum trichloride. However, the process is suitable to only a very limited extent for the preparation of compounds of formula I wherein $R_3$ is chlorine. For example, in the reaction of methylene dibenzoate, chloromethyl benzoate was isolated in a yield of only about 50%. When methylene diacetate was used as starting material, the reaction mixture comprised about 40 mol-% chloromethyl acetate, as was determined by evaluation of the $^1$H-NMR spectrum, but that product could not be isolated. A further disadvantage is that mixtures of oligo- and poly-silanols are always formed in an equimolar amount as undesired by-products which are volatilized only with difficulty and which can be disposed of on an industrial scale only at great expense.

The invention was therefore based on the hitherto unsolved problem of developing a process for the preparation of compounds of formula I that avoids the disadvantages of the known processes. This problem is solved very well by the process according to the invention.

The process according to the invention is based on the discovery, which is surprising in the light of the prior art, that, instead of using as halogen donor special reagents that are highly toxic and/or difficult to handle, it is possible to use a hydrogen halide of formula III, without the yield, reaction velocity and product purity being impaired, and that the formation of bis($\alpha$-haloalkyl)ethers can be very largely avoided in that manner. For example, the Example of operation shows that approximately 100 times less bis(chloromethyl)ether is formed according to the invention than is the case with the already optimised known procedure according to the Comparison Example. A further advantage is that the reaction is very easily monitored, and fewer by-products are formed.

The reaction is generally carried out using at least an equimolar amount of a hydrogen halide of formula III (referring to the molar amount of the compound of formula II), in the presence or absence of solvents or diluents, advantageously at elevated temperature and with subsequent working up by distillation.

The reaction is preferably carried out in the presence of a Lewis acid as catalyst under atmospheric pressure or elevated pressure, or in the absence of a Lewis catalyst under atmospheric pressure or, advantageously, under elevated pressure. The pressure may especially be up to 250 bar, very especially up to 50 bar, for example up to 10 bar.

Greater preference is given to the reaction in the presence of a Lewis acid, which is carried out under a slight excess pressure if necessary.

According to the invention there are used as Lewis acids catalytic amounts, for example, referring to the molar amount of the compound of the formula II, from approximately 0.01 to approximately 0.1 times, such as approximately 0.02 to approximately 0.05 times, that molar amount, of a halide of a metal of groups IIb, IIIb and IVb of the periodic system of the elements, such as appropriate zinc, tin, zirconium and aluminium halides, especially zinc halides of the formula $Zn(R_3)_2$ (X).

There come into consideration as solvents, for example, haloalkanes or haloaromatic compounds, such as di-, tri- or tetra-chloro-$C_1$-$C_4$alkanes, for example methylene chloride, trichloroethane or chlorobenzene. Advantageously, however, the reaction according to the invention may be carried out without a solvent, in which case the hydrogen halide of formula III is introduced in the gaseous state of aggregation, if necessary under a slight excess pressure, for example under an excess pressure of approximately from 10 to 100 mbar, especially from approximately 10 to approximately 30 mbar.

Advantageously, referring to the molar amount of the compound of the formula II, a slight excess, for example from approximately 1.05 to approximately 1.75 times, such as from approximately 1.05 to approximately 1.5 times, especially from approximately 1.05 to approximately 1.15 times that molar amount, of hydrogen halide is used.

The reaction is advantageously carried out at elevated temperature, preferably in a temperature range of from 0° C. to 150° C., for example from approximately 40° C. to approximately 120° C., e.g. approximately from 50° C. to 100° C., such as from approximately 50° C. to approximately 100° C., especially approximately from 50° C. to 80° C., with a temperature of approximately 60° C. being especially preferred.

The separation of the reaction product by distillation is advantageously carried out under reduced pressure, for example at from approximately 1 mbar to approximately 50 mbar, especially at from approximately 10 mbar to approximately 30 mbar.

In a preferred form of the process according to the invention, a mixture of an acylal of formula II and approximately 0.02 to 0.05 times the molar amount of a zinc halide of formula IX is heated to approximately from 50° C. to 70° C., an excess of approximately 1.05 to approximately 1.5 times, especially approximately 1.05 to approximately 1.15 times, the molar amount of hydrogen halide is introduced over a period of approximately from 2 to 10 hours, especially approximately from 4 to 6 hours, and the reaction mixture is distilled under reduced pressure, for example at from approximately 10 mbar to approximately 30 mbar.

The starting materials of formula II are known or are prepared according to processes known per se.

For example, the acylals (aldehyde acylates) of formula II can be prepared according to one of the processes mentioned in "Houben-Weyl-Methoden der organischen Chemie", E. Müller et al. (eds.), Vol. 7, Part 1, 4th edition, Georg Thieme Verlag, Stuttgart, p. 442, or according to Kochhar et al., J. Org. Chem. 48, 1765 (1983), Olah et al., Synthesis p. 962, (1982) or Michie et al., Synthesis p. 824, (1981).

The following Examples serve to illustrate the invention; temperatures are given in degrees Celsius, pressures in mbar.

EXAMPLE OF OPERATION 216 g of methylene dipivalate (II; $R_1$ = tert-butyl, $R_2$ = hydrogen) are heated to approximately 60°, and 4.5 g of zinc chloride are added. A total of 38.5 g of hydrogen chloride are then introduced within a period of 5 hours, with stirring. The composition of the reaction mixture is determined in an aliquot sample. The reaction balance is as follows:

| | |
|---|---|
| 143.0 g | chloromethyl pivalate |
| 4.5 g | zinc chloride |
| 96.9 g | pivalic acid |
| 0.4 g | bis(chloromethyl)ether |
| 10.0 g | methylene dipivalate |

The reaction mixture is then hydrolysed by the addition of a small amount of water and separated by distillation under reduced pressure (approximately 20 mbar); there is obtained at least 99% pure chloromethyl pivalate which comprises less than 0.1 ppm of the toxic bis(chloromethyl)ether, in a yield of 95% of the theoretical yield.

COMPARISON EXAMPLE 1.7 g of zinc chloride are stirred with 0.8 ml of water, and 180.0 g of thionyl chloride are added carefully, with stirring. The mixture is then stirred for one hour at room temperature, and then a suspension of 42.1 g of paraformaldehyde in 85.0 g of molten pivalic acid is added in portions at 70°, with stirring. The mixture is heated at 100° for one hour, with stirring. In the course of the reaction a total of 36.5 g of hydrogen chloride and 80 g of sulfur dioxide are freed. The composition of the reaction mixture is determined in an aliquot sample. The reaction balance, taking account of the volatile constituents collected separately, is as follows:

| | |
|---|---|
| 106.5 g | chloromethyl pivalate |
| 80.0 g | sulfur dioxide |
| 13.0 g | pivalic acid chloride |
| 30.0 g | thionyl chloride |
| 52.0 g | bis(chloromethyl)ether |
| 36.5 g | hydrogen chloride |
| 1.7 g | zinc chloride |

The reaction mixture is separated by distillation under reduced pressure (approximately 20 mbar); there is obtained approximately 99% pure chloromethyl pivalate, in a yield of 85.2% of the theoretical yield.

What is claimed is:

1. A process for the preparation of halogenated carboxylic acid esters of formula I

wherein $R_1$ is alkyl, alkenyl, alkynyl, cycloalkyl, aralkyl or aryl, $R_2$ hydrogen is alkyl or cycloalkyl, and $R_3$ is halogen having an atomic number of from 9 up to and including 53, which process comprises reacting an acylal of formula II

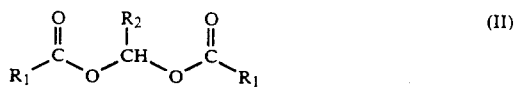

with a hydrogen halide of the formula

2. A process according to claim 1, wherein the reaction is carried out in the presence of a Lewis acid.

3. A process according to claim 1, wherein the acylal of formula II is reacted with at least an equimolar amount of a hydrogen halide of formula III.

4. A process according to claim 1, wherein, referring to the molar amount of the acylal of the formula II, a 1.05- to 1.75-fold molar excess of the hydrogen halide of formula III is used.

5. A process according to claim 1, wherein the reaction is carried out in a temperature range of from 0° C. to 150° C.

6. A process according to claim 1, wherein, referring to the molar amount of the acylal of the formula II, there is used a catalytic 0.01- to 0.1-fold molar amount of a halide of a metal of groups IIb, IIIb and IVb of the periodic system of the elements as Lewis acid.

7. A process according to claim 1, wherein, referring to the molar amount of the acylal of the formula II, a 1.05- to 1.75-fold molar excess of the hydrogen halide of formula III is used, a catalytic 0.01- to 0.1-fold molar amount of a halide of a metal of groups IIb, IIIb and IVb of the periodic system of the elements is used as Lewis acid, and the reaction is carried out in a temperature range of from 0° C. to 150° C.

8. A process according to claim 1, wherein the separation of the reaction product by distillation is carried out under reduced pressure of from 1 mbar to 50 mbar.

9. A process according to claim 1, wherein the starting materials are so selected that there are prepared compounds of formula I wherein $R_1$ is $C_1-C_{14}$alkyl, $C_2-C_7$alkenyl, $C_3-C_7$-alkynyl, or 3- to 8-membered cycloalkyl; or is phenyl or naphthyl each of which is unsubstituted or substituted by $C_1-C_4$alkyl, $C_1-C_4$alkoxy, halogen, trifluoromethyl and/or by nitro, or mono-, di- or tri-phenyl-$C_1-C_4$alkyl that is unsubstituted or substituted in the phenyl moiety by $C_1-C_4$alkyl, $C_1-C_4$alkoxy, halogen, trifluoromethyl and/or by nitro, $R_2$ hydrogen is $C_1-C_7$alkyl or 3- to 8-membered cycloalkyl, and $R_3$ is halogen having an atomic number of from 9 up to and including 53.

10. A process according to claim 7, wherein the starting materials are so selected that there are prepared compounds of formula I wherein $R_1$ is $C_1-C_{14}$alkyl, $C_2-C_7$alkenyl, $C_3-C_7$alkynyl, or 3- to 8-membered cycloalkyl; or is phenyl or naphthyl each of which is unsubstituted or substituted by $C_1-C_4$alkyl, $C_1-C_4$alkoxy, halogen, trifluoromethyl and/or by nitro, or mono-, di- or tri-phenyl-$C_1-C_4$alkyl that is unsubstituted or substituted in the phenyl moiety by $C_1-C_4$alkyl, $C_1-C_4$alkoxy, halogen, trifluoromethyl and/or by nitro, $R_2$ hydrogen is $C_1-C_7$alkyl or 3- to 8-membered cycloalkyl, and $R_3$ is halogen having an atomic number of from 9 up to and including 53.

11. A process according to claim 1, wherein the starting materials are so selected that there are prepared compounds of formula I wherein $R_1$ is $C_1-C_7$alkyl, $R_2$ is hydrogen or $C_1-C_4$alkyl, and $R_3$ is chlorine or bromine.

12. A process according to claim 1, wherein the starting materials are so selected that there are prepared compounds of formula I wherein $R_1$ is methyl, ethyl or secondary-linear or branched $C_3-C_7$alkyl, $R_2$ is hydrogen and $R_3$ is chlorine.

13. A process according to claim 1, wherein the starting materials are so selected that chloromethyl pivalate (I; $R_1$=tert-butyl, $R_2$=hydrogen, $R_3$=chlorine) is prepared.

14. A process according to claim 1, wherein chloromethyl pivalate (of formula I; $R_1$=tert-butyl, $R_2$=hydrogen) is prepared by heating methylene dipivalate (of formula II; $R_1$=tert-butyl, $R_2$=hydrogen) to approximately 60° C., adding 0.033 mol of zinc chloride per mol of methylene dipivalate, introducing within a period of 5 hours 1.057 mol of hydrogen chloride per mol of chloromethyl pivalate, then hydrolysing the reaction mixture by the addition of a small amount of water, and separating the reaction mixture by distillation at approximately 20 mbar.

* * * * *